United States Patent [19]

Handa et al.

[11] 4,074,052

[45] Feb. 14, 1978

[54] PROCESS FOR PREPARATION OF ISOCYANURIC ACID TRIESTERS

[75] Inventors: Susumu Handa, Wakayama; Yoshiaki Tanaka, Osaka; Atsushi Nishihata, Wakayama; Sadashi Ueda, Wakayama; Yoshiaki Inamoto, Wakayama; Fumio Tanimoto, Kyoto; Hisao Kitano, Osaka, all of Japan

[73] Assignee: Kao Soap Co., Ltd., Tokyo, Japan

[21] Appl. No.: 749,053

[22] Filed: Dec. 9, 1976

[30] Foreign Application Priority Data

Jan. 19, 1976 Japan ................................. 51-4828

[51] Int. Cl.$^2$ : .......................................... C07D 251/34
[52] U.S. Cl. .................................................. 544/221
[58] Field of Search .................. 260/248 NS; 544/221

[56] References Cited

U.S. PATENT DOCUMENTS 3,088,948   5/1963   Little et al. ................... 260/248 NS

OTHER PUBLICATIONS

Paoloni et al., *J. Hetero Chem.*, vol. 5, pp. 533-544 (1968).

*Primary Examiner*—John M. Ford
*Attorney, Agent, or Firm*—Blanchard, Flynn, Thiel, Boutell & Tanis

[57] ABSTRACT

Isocyanuric acid triesters are prepared by isomerization of the corresponding cyanuric acid triesters. The starting cyanuric acid esters are dissolved in a polar solvent which is free of active hydrogen atoms, which contains a nitrogen or sulfur atom in the molecule and which has a boiling point not higher than 260° C. The solution may optionally contain an alkali metal halide, an alkaline earth metal halide or an ammonium halide. Isomerization is carried out at a temperature of from 50° to 200° C.

13 Claims, No Drawings

PROCESS FOR PREPARATION OF ISOCYANURIC ACID TRIESTERS

BACKGROUND OF THE INVENTION

1. Field of the Invention

The present invention relates to a process for the preparation of isocyanuric acid triesters.

It is a primary object of the present invention to provide a process according to which isocyanuric acid triesters, which are useful in various industries such as the chemical industry, the resin industry and the paint industry, can easily be prepared with economic advantages. The process of the present invention can be used to prepare various known useful isocyanuric acid triesters.

The isocyanuric acid triesters that can be prepared according to the process of the present invention include all isocyanuric acid triesters except triaryl isocyanurates. The process of the present invention is especially preferred for the preparation of trialkyl isocyanurates and triaralkyl isocyanurates.

2. Description of the Prior Art

Isocyanuric acid triesters have previously been used as starting materials for preparing heat-resistant resins, modifiers, additives and the like, but the specific esters that are actually used on an industrial scale are limited in number and they are quite expensive. Accordingly, these esters are not manufactured in large quantities.

As conventional methods for the preparation of these isocyanuric acid triesters, there can be mentioned, for example, (1) a method in which a corresponding organic isocyanic acid ester is trimerized, (2) a method in which a corresponding organic halogen compound is subjected to substitution reaction with an alkali cyanate and then the resulting isocyanic acid ester is trimerized and (3) a method in which a corresponding organic halogen compound is subjected to substitution reaction with cyanuric chloride. According to the method (1), isocyanuric acid triesters can be prepared most easily, but this method (1) is disadvantageous because the isocyanic acid esters that are now industrially available are very expensive and few in number. In each of the methods (2) and (3), an organic halogen compound is used as the starting material. Since the reactivity of the organic halogen compound to the intended substitution reaction is very low, the isocyanuric acid triesters that can be prepared according to these methods (2) and (3) are limited to a few triesters, for example, triallyl isocyanurate.

SUMMARY OF THE INVENTION

We have discovered a versatile and valuable process for the preparation of isocyanuric acid triesters, which process can be used to prepare all isocyanuric acid triesters, except triaryl isocyanurates.

More specifically, we found that when a cyanuric acid triester having the following formula:

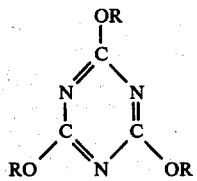

wherein R is alkyl, alkenyl, alkynyl or aralkyl, is heated at 50° to 200° C, in the presence or absence of an alkali metal halide, an alkaline earth metal halide or an ammonium halide, in a polar solvent which is free from any active hydrogen atoms but which contains a nitrogen or sulfur atom in the molecule and has a boiling point not higher than 260° C. The cyanuric acid triester is thereby isomerized to an isocyanuric acid triester having the following general formula:

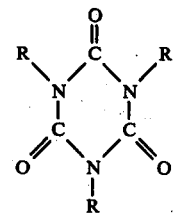

wherein R has the same meaning as defined above, whereby such isocyanuric acid triester can easily be prepared.

It is known that cyanuric acid trialkyl esters are converted to isocyanuric acid trialkyl esters by thermal isomerization, and trimethyl isocyanurate has previously been prepared by this process. However, in the isomerization utilizing heat alone, because the reaction advances only in the molten state, the reactant must be kept in the molten state during the reaction. Therefore, the process involves handling and operational difficulties and, in general, a high temperature exceeding 200° C and a long time are required for the reaction (L. Paoloni et al., J. Heterocycl. Chem., 5, 533–544 (1968)). Moreover, since there has been no suitable industrial process for the production of the starting cyanuric triesters, isocyanuric acid triesters have scarcely been produced by the isomerization process.

Recently, however, there has been developed a process for preparing cyanuric acid triesters with ease at low cost. More specifically, lower triesters of cyanuric acid can be prepared in good yields by reacting cyanuric chloride with an alcohol in the presence of an alkali (James R. Dudley et al., J.A.C.S., 73, 2986–2990 (1951)). Further, since cyanuric acid trialkyl esters can easily undergo an ester exchange reaction, they can easily be converted to various cyanuric acid triesters.

According to the process of the present invention, it was found that cyanuric acid triesters can be isomerized simply by heating a solution of same dissolved in a specific class of polar solvents, at from about 50° to about 200° C, preferably at from about 100° to about 170° C, in the presence or absence of a catalyst such as an alkali metal chloride. Isocyanuric acid triesters can easily be prepared by this process. Especially in case of trimethyl cyanurate, simply by heating a solution of same in dimethylformamide, at about 100° C, isomerization is completed in several hours and the trimethyl cyanurate is converted to trimethyl isocyanurate substantially completely.

The term "cyanuric acid triester" referred to in the instant specification includes trialkyl esters of cyanuric acid, trialkenyl esters of cyanuric acid, trialkynyl esters of cyanuric acid, and triaralkyl esters of cyanuric acid. These esters can have, in the ester moiety, substituents such as alkyl, phenyl, nitrile, alkoxy and halogen and such compounds are also included. The trialkyl esters preferably have from one to 4 carbon atoms in the alkyl group. The trialkenyl esters preferably have from 2 to 4 carbon atoms in the alkenyl group, such as allyl. The trialkynyl esters preferably have from 2 to 4 carbon atoms in the alkynyl group, such as propargyl. The triaralkyl esters preferably have from 7 to 11 carbon atoms in the aralkyl group, such as benzyl and alkyl-substituted benzyl.

Various cyanuric acid triesters are important from the industrial viewpoint, and typical examples are mentioned below (where appropriate, these compounds include those having substituents distinguished by prefixes such as normal, secondary, iso, tertiary, ortho, meta and para):

Trimethyl cyanurate, triethyl cyanurate, tributyl cyanurate, triallyl cyanurate, tripropargyl cyanurate, tribenzyl cyanurate, tri(methylbenzyl) cyanurate, etc.

The term "polar solvent which is free of any active hydrogen atoms and contains a nitrogen or sulfur atom in the molecule and has a boiling point not higher than 260° C" referred to in the instant specification means compounds having a dielectric constant of at least 15. These polar compounds can be used singly, or in the form of a mixture of two or more of these polar compounds, or in the form of a mixture containing as the main component such polar compound mixed with an organic solvent which is free of any active hydrogen atoms as a second solvent component. The second solvent is non-polar. Examples of the polar organic solvent are as follows:

Dimethylformamide, diethylformamide, dimethylacetamide, diethylacetamide, N-methylpyrrolidone, N-ethylpyrrolidone, tetramethylurea, N-formylmorpholine, N-acetylmorpholine, N-formylpiperidine, N-acetylpiperidine, dimethylsulfoxide, diethylsulfoxide, dimethylsulfone, diethylsulfone, tetramethylenesulfoxide, tetramethylenesulfone, hexamethylphosphotriamide, etc.

Of these solvents, dimethylformamide, diethylformamide, dimethylacetamide, N-methylpyrrolidone, tetramethylurea, dimethylsulfoxide, dimethylsulfone and hexamethylphosphotriamide are important from the industrial viewpoint.

The organic solvent that is used as the optional second component of the polar solvent composition in the present invention must be selected from those that are free of any active hydrogen atoms. As such organic solvent, there can be mentioned, for example, hydrocarbons, halogenated hydrocarbons, ketones, ethers, nitrated hydrocarbons and nitriles. When such second solvents are used by themselves, the rate of isomerization of the cyanuric acid triesters is very low and the use of such second solvents, by themselves, is not within the scope of this invention. It is important that when such second organic solvent is used in combination with the preferred polar solvent of the present invention, the amount of such second organic solvent must be less than 50% by weight, based on the weight of the polar solvent.

It is known that halogenated hydrocarbons have an isomerizing activity even when used alone (see the specification of U.S. Pat. No. 3,075,979). It was found that when such halogenated hydrocarbon is added to the polar solvent of the present invention in a minor amount (about 10% by weight), the isomerizing effect can be remarkably enhanced.

As the alkali metal halides, alkaline earth metal halides and ammonium halides that can be used in the present invention, there can be mentioned, for example, lithium chloride, sodium chloride, potassium chloride, rubidium chloride, cesium chloride, beryllium chloride, magnesium chloride, calcium chloride, strontium chloride, barium chloride, ammonium chloride, and the corresponding bromides and iodides. Since the bromides and iodides have a higher solubility in the polar solvent than the chlorides, they have a higher catalytic activity. Among these halides, lithium chloride, calcium chloride, ammonium chloride and potassium bromide are especially useful from the industrial viewpoint. These halides are used in amounts of from 0.1 to 100 mole %, preferably 1 to 50 mole %, based on the starting cyanuric acid triester.

Triaryl cyanurates cannot be isomerized according to the process of the present invention. The present invention does not include isomerization of triaryl esters of cyanuric acid.

The preparation of the isocyanuric acid triesters according to the present invention is represented by the following reaction scheme:

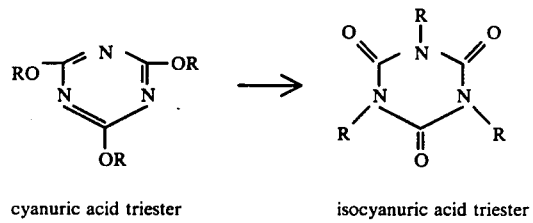

cyanuric acid triester      isocyanuric acid triester

This reaction is carried out at a temperature of from 50° to 200° C, preferably 100° to 170° C, in a polar solvent such as those mentioned above. The polar solvent is used in an amount sufficient to dissolve the starting cyanuric acid triester and the isocyanuric acid triester isomerization reaction product. In general, the polar solvent is used in an amount from 2 to 20 times, especially about 5 times, the amount of the starting cyanuric acid triester on a weight basis.

Separation of the reaction product from the reaction mixture can be accomplished simply by removing the solvent and the halide used as the catalyst from the reaction mixture (which can be transferred directly to the next process for reuse, according to need) when the isomerization is completed. Since the cyanuric acid triester starting material is considerably different from the isocyanuric acid triester final product with respect to their physical properties such as the melting point, boiling point and solubility, even if the isomerization is incomplete, separation of the final product from the starting material can be accomplished very easily by employing appropriate known separation methods such as distillation, filtration, crystallization, precipitation, centrifugal separation, extraction and water washing. The manner of combining these separation methods and the order of these methods are appropriately selected depending on the properties of the starting cyanuric acid triester and the isocyanuric acid triester final product.

We have made various experiments in connection with the above-mentioned process of the present invention and we have confirmed the excellent effects and advantages attained by the present invention based on these experiments. Typical illustrative Examples are described hereinafter for better illustration of the technical content of the present invention. However, it will be understood that the scope of the present invention is not limited by these Examples.

Synthesis of Starting Cyanuric Acid Triester

Tribenzyl cyanurate was prepared according to the above-mentioned method taught by J. R. Dudley et al.

In 940 ml of benzyl alcohol there was dissolved 144 g (3.35 moles) of sodium hydroxide at a temperature ranging from room temperature to 40° C, and 184 g (1.0 mole) of cyanuric chloride was added to the solution with agitation and cooling to 25° to 30° C over a period of 1 hour and 40 minutes. Then, 500 ml of benzene was added and the reaction was conducted for 2 hours. The reaction mixture was neutralized with hydrochloric acid and the resulting sodium chloride was removed by filtration. Benzene and excess benzyl alcohol was stripped from the filtrate under a vacuum of 10 mm Hg at an elevated temperature of 93° C. There was obtained 373 g of crude tribenzyl cyanurate having a melting point of 95° to 100° C. The yield was 94% based on the cyanuric chloride. Recrystallization from ethanol gave colorless needles having a melting point of 104.5° to 105.6° C. The results of the elementary analysis were as follows:

Found: C = 72.2%, H = 5.2%, N = 10.4%, O = 12.0%. Calculated: (for $C_{24}H_{21}N_3O_3$) C = 72.18%, H = 5.26%, N = 10.53%, O = 12.03%.

In the infrared absorption spectrum, absorptions inherent of th S-trazine skeleton were observed at 1565, 1340 and 810 cm$^{-1}$ and an absorption inherent of the ether linkage was observed at 1125 cm$^{-1}$. However, there were observed none of the absorptions inherent of the S-triazine-trione skeleton at 1690, 1450 and 750 cm$^{-1}$.

In the same manner as described above, trimethyl cyanurate (having a melting point of 135° to 137° C; the yield being 92%) was synthesized. Further, triphenyl cyanurate (having a melting point of 241° C) was synthesized by the reaction, under molten conditions, between phenol and cyanuric chloride.

EXAMPLE 1

In a mixed solvent of 230 ml of dimethylformamide and 30 ml of benzyl chloride, there was dissolved 40 g of tribenzyl cyanurate, and the isomerization reaction was carried out at 140° C for 2 hours in a dry nitrogen atmosphere. The dimethylformamide and benzyl chloride were stripped from the reaction mixture under reduced pressure. Recrystallization of the resulting crude product from ethanol/acetone gave crystals of I (dry weight = 24.3 g; 61% by weight based on the starting tribenzyl cyanurate), and concentration of the mother liquor gave crystals II (dry weight = 10.9 g; 27% by weight based on the starting tribenzyl cyanurate). The residual mother liquor was concentrated to dryness thereby to obtain a greasy residue (4.8 g; 12% by weight based on the starting tribenzyl cyanurate). The crystals I had a melting point of 163° to 164° C, and in the infrared absorption spectrum of the crystals I, the absorption inherent of the S-triazine skeleton was extinguished, but intense absorptions inherent of the S-triazine-trione skeleton were observed at 1690, 1450 and 750 cm$^{-1}$. The absorption spectrum of the crystals I was in good agreement with that of tribenzyl isocyanurate (having a melting point of 161° to 162° C) synthesized separately. From the results of the proton NMR analysis of the methylene proton of the benzyl group, it was found that the purity of the crystals I was 98% (the remainder being tribenzyl cyanurate). From the results of the NMR analysis of the crystals II (having a melting point of 97.5° to 99.0° C) and the residue, it was found that they contained 13 and 17%, respectively, of tribenzyl isocyanurate. The total amount of tribenzyl isocyanurate contained in the crystals I and II and the residue was 26.4 g, and the isomerization ratio was 66%.

The proton NMR was carried out in the following manner:

A 10% solution of the sample in deuterio-chloroform was prepared, and the measurement was conducted at 60 MHz by using tetramethylsilane as the internal standard. The chemical shifts ($\delta$) of the methylene protons of tribenzyl cyanurate and tribenzyl isocyanurate were at 5.40 ppm and 4.96 ppm, respectively.

When the reaction was carried out for 7 hours under the same conditions as described above, the starting triester was completely isomerized to tribenzyl isocyanurate.

COMPARATIVE EXAMPLE 1

Tribenzyl cyanurate (40 g) was heated and melted at 180° C for 3 hours in the absence of a solvent in a dry nitrogen atmosphere. The product was recrystallized from ethanol/dimethylformamide to divide it into a crystal fraction (dry weight = 18.9 g; 47% by weight based on the starting tribenzyl cyanurate) and a greasy fraction (21.1 g; 53% by weight based on the starting tribenzyl cyanurate). From the results of the infrared absorption spectrum analysis and the proton NMR analysis, it was found that the crystal fraction (having a melting point of 163° to 163.5° C) was tribenzyl isocyanurate having a purity of 100%, the greasy fraction contained 30% of tribenzyl isocyanurate, and the total isomerization ratio was 63%.

When the melting reaction was carried out at 200° C for 3 hours, the isomerization ratio was 89%, and in order to obtain an isomerization ratio of 100%, the melting reaction had to be carried out at 200° C for 5 hours.

EXAMPLE 2

In 0.15 mole of a solvent as set forth in Table 1, 2.0 g (0.005 mole) of tribenzyl cyanurate was reacted at 140° to 160° C. Sampling was appropriately conducted, and the sample was directly subjected to the proton NMR analysis (tetramethylsilane was used as the internal standard) and the isomerization ratio was determined by utilizing the chemical shift ($\delta$) of the methylene proton. Since the rate of the isomerization reaction is in proportion to the concentration of the cyanuric acid triester substantially linearly for a conversion up to about two-thirds, the rate of the isomerization reaction was evaluated based on the half-life of tribenzyl cyanurate, that is, the time required for the concentration of the tribenzyl cyanurate to be reduced to one-half the starting concentration. The results are shown in Table 1. For comparison, the above reaction was carried out in the same manner as above by using diethyleneglycol dimethyl ether and xylene as solvents having a low polarity, which are outside the scope of the present invention. The results obtained are shown in Table 1.

Table 1

| Solvent | Boiling Point (° C) | Chemical Shift, δ (ppm) of Methylene Proton of Tribenzyl Ester | | Half-life of Tribenzyl Cyanurate | |
|---|---|---|---|---|---|
| | | Cyanuric Acid | Isocyanuric Acid | Reaction Temperature (° C) | Time (hours) |
| dimethylformamide | 153 | 5.50 | 5.05 | 150 | 9 |
| dimethylacetamide | 166 | 5.49 | 5.03 | 160 | 13 |
| tetramethylurea | 177 | 5.48 | 5.01 | 160 | 15 |
| N-methylpyrrolidone | 202 | 5.50 | 4.98 | 160 | 10 |
| hexamethylphosphorictriamide | 233 | 5.49 | 4.98 | 160 | 1.75 |
| diethyleneglycol dimethyl ether | 162 | 5.41 | 5.00 | 160 | not changed in 10 hours |
| p-xylene | 138 | 5.20 | 4.68 | 138 | not changed in 10 hours |

EXAMPLE 3

In a mixed solvent dimethylformamide/benzyl chloride having a mixing ratio (mole/mole) as shown in Table 2, 0.005 mole (2.0 g) of tribenzyl cyanurate was reacted at 141° C. In the same manner as described in Example 2, the isomerization reaction rate was evaluated based on the half-life period of tribenzyl cyanurate. The results obtained are shown in Table 2.

Table 2

| Mixed Solvent | | Reaction Temperature (° C) | Half-life Period (hours) of Tribenzyl Cyanurate |
|---|---|---|---|
| Dimethylformamide (mole) | Benzyl Chloride (mole) | | |
| 0.15 | 0.005 | 141 | 1.75 |
| 0.15 | 0.015 | 141 | 2 |
| 0.15 | 0.045 | 141 | 2.17 |
| 0.075 | 0.075 | 141 | 3 |
| 0.045 | 0.15 | 141 | 5 |
| 0.005 | 0.135 | 141 | 19 |

EXAMPLE 4

In 12 ml of dimethylformamide was dissolved 2.0 g of tribenzyl cyanurate, and a halogen compound as listed in Table 3 was added. The isomerization reaction was carried out at 150° C. In the same manner as described in Example 2, the half-life period of tribenzyl cyanurate was measured. The results obtained are shown in Table 3. In Table 3, the amount added of the halogen compound is expressed in terms of mole %, based on tribenzyl cyanurate.

Table 3

| Halogen Compound | Amount (mole %) Added of Halogen Compound | State of Reaction Mixture at Reaction Temperature | Half-life Period of Tribenzyl Cyanurate | |
|---|---|---|---|---|
| | | | Reaction Temperature (° C) | Time (minutes) |
| lithium chloride | 2 | homogeneous | 150 | 195 |
| " | 10 | " | 150 | 45 |
| " | 50 | " | 150 | 15 |
| sodium chloride | 10 | heterogeneous | 150 | 220 |
| potassium chloride | 10 | " | 150 | 255 |
| potassium bromide | 10 | " | 150 | 60 |
| potassium iodide | 10 | homogeneous | 150 | 40 |
| calcium chloride | 10 | " | 150 | 50 |
| ammonium chloride | 10 | heterogeneous | 150 | 100 |

EXAMPLE 5

In 10 ml of dimethylformamide, 1.1 g of trimethyl cyanurate was isomerized at 100° C for 2 hours. The reaction mixture was directly subjected to proton NMR analysis (using tetramethylsilane as the internal standard), and it was found that 87% of trimethyl cyanurate was isomerized to trimethyl isocyanurate (the chemical shifts (δ) of the methyl protons of the cyanuric acid and isocyanuric acid esters were at 4.00 ppm and 3.30 ppm, respectively). The product left after stripping the dimethylformamide from the reaction mixture was subjected to infrared absorption analysis, and it was found that absorptions inherent of the S-triazine skeleton at 1570 and 800 cm$^{-1}$ were substantially extinguished but intense absorptions inherent of the S-triazine-trione skeleton were observed at 1680, 1470 and 750 cm$^{-1}$ instead. When the reaction was carried out at 140° C, isomerization was completed in 1 hour.

The embodiments of the invention in which an exclusive property or privilege is claimed are defined as follows:

1. A process of preparing an isocyanuric acid triester, which comprises the steps of heating at a temperature of from 50° to 200° C, a solution of a cyanuric acid triester having the formula

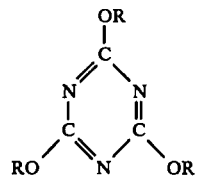

wherein R is alkyl, alkenyl, alkynyl or aralkyl, dissolved in a solvent comprising a liquid polar organic substance having a dielectric constant of at least 15 which is free of active hydrogen atoms and contains a nitrogen or sulfur atom in the molecule and has a boiling point not higher than 260° C, to effect a liquid phase isomerization of said cyanuric acid triester to the corresponding isocyanuric acid triester; and recovering said isocyanuric acid triester from the reaction mixture.

2. A process according to claim 1 in which said solvent consists essentially of a polar substance selected from the group consisting of dimethylformamide, diethylformamide, dimethylacetamide, diethylacetamide, N-methylpyrrolidone, N-ethylpyrrolidone, tetramethylurea, N-formylmorpholine, N-acetylmorpholine, N-formylpiperidine, N-acetylpiperidine, dimethylsulfoxide, diethylsulfoxide, dimethylsulfone, diethylsulfone, tetramethylenesulfoxide tetramethylenesulfone, hexamethylphosphotriamide and mixtures thereof.

3. A process according to claim 2 in which said solvent also contains up to 50 weight percent, based on the weight of said polar substance, of a different liquid organic solvent which also is free of any active hydrogen atoms.

4. A process according to claim 1 in which the weight of said polar organic substance is from 2 to 20 times the weight of said cyanuric acid triester.

5. A process according to claim 1 in which the isomerization reaction temperature is from 100° to 170° C.

6. A process of preparing an isocyanuric acid triester, which comprises the steps of heating at a temperature of from 50° to 200° C, a solution of a cyanuric acid triester having the formula

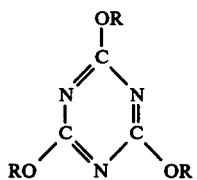

wherein R is alkyl, alkenyl, alkynyl or aralkyl, dissolved in a solvent comprising a liquid polar organic substance having a dielectric constant of at least 15 which is free of active hydrogen atoms and contains a nitrogen or sulfur atom in the molecule and has a boiling point not higher than 260° C, said solution containing dissolved or dispersed therein an effective catalytic amount of a catalyst substance selected from the group consisting of alkali metal halides, alkaline earth metal halides, ammonium halides and mixtures thereof, to effect a liquid phase isomerization of said cyanuric acid triester to the corresponding isocyanuric acid triester; and recovering said isocyanuric acid triester from the reaction mixture.

7. A process according to claim 6 in which said solvent consists essentially of a polar substance selected from the group consisting of dimethylformamide, diethylformamide, dimethylacetamide, diethylacetamide, N-methylpyrrolidone, N-ethylpyrrolidone, tetramethylurea, N-formylmorpholine, N-acetylmorpholine, N-formylpiperidine, N-acetylpiperidine, dimethylsulfoxide, diethylsulfoxide, dimethylsulfone, diethylsulfone, tetramethylenesulfoxide, tetramethylenesulfone, hexamethylphosphotriamide and mixtures thereof.

8. A process according to claim 7 in which said solvent also contains up to 50 weight percent, based on the weight of said polar substance, of a different liquid organic solvent which is free of any active hydrogen atoms.

9. A process according to claim 6 in which the weight of said polar organic substance is from 2 to 20 times the weight of said cyanuric acid triester.

10. A process according to claim 6 in which the isomerization reaction temperature is from 100° to 170° C.

11. A process according to claim 6 in which the amount of said catalyst is from 0.1 to 100 mole percent, based on the number of moles of said cyanuric acid triester.

12. A process according to claim 6 in which the amount of said catalyst is from 1 to 50 mole percent, based on the number of moles of said cyanuric acid triester.

13. A process according to claim 12 in which said catalyst is selected from the group consisting of lithium chloride, sodium chloride, potassium chloride, rubidium chloride, cesium chloride, beryllium chloride, magnesium chloride, calcium chloride, strontium chloride, barium chloride, ammonium chloride, and the corresponding bromides and iodides.

* * * * *